United States Patent
Register

[19]

[11] Patent Number: 5,962,048
[45] Date of Patent: Oct. 5, 1999

[54] VETERINARY PHARMACEUTICAL METHOD OF ADMINISTRATION

[76] Inventor: Jack W. Register, 1513 5th Ave. East, Menomonie, Wis. 54751

[21] Appl. No.: 08/969,042

[22] Filed: Nov. 12, 1997

Related U.S. Application Data

[63] Continuation-in-part of application No. 08/599,021, Feb. 8, 1996.

[51] Int. Cl.$^6$ .................................................... A23K 1/175
[52] U.S. Cl. ................................. 426/74; 426/72; 426/73
[58] Field of Search .................................. 426/72, 73, 74

[56] References Cited

U.S. PATENT DOCUMENTS

| | | | |
|---|---|---|---|
| 3,658,549 | 4/1972 | Geiersberger et al. | 99/2 CD |
| 3,794,740 | 2/1974 | Achorn et al. | 426/69 |
| 4,786,510 | 11/1988 | Nakel et al. | 426/74 |
| 4,994,283 | 2/1991 | Mehansho et al. | 426/74 |
| 4,994,284 | 2/1991 | Miller | 426/74 |
| 5,002,779 | 3/1991 | Mehansho et al. | 426/72 |
| 5,232,709 | 8/1993 | Saltman et al. | 424/630 |
| 5,360,823 | 11/1994 | Griffel, Jr. et al. | 514/706 |
| 5,393,535 | 2/1995 | Kjems | 424/678 |
| 5,456,927 | 10/1995 | Vinci et al. | 426/74 |
| 5,601,836 | 2/1997 | Parker | 424/438 |
| 5,609,897 | 3/1997 | Chandler et al. | 426/73 |
| 5,698,222 | 12/1997 | Mazer et al. | 424/464 |

*Primary Examiner*—Terressa Mosley
*Attorney, Agent, or Firm*—Skinner and Associates

[57] ABSTRACT

A composition for preventing and treating milk fever in freshening cows, and a method of administering the composition. The basic composition is a mixture of water, calcium chloride, propylene glycol, B vitamins and minerals. The calcium content is lower than conventional calcium treatments used for this purpose. The propylene glycol gives the cow an energy boost and sweetens the taste so the cow does not object to it as it does to conventional gels and liquids. The B vitamins stimulate the cow's appetite. The minerals replace minerals lost in the milk and also help the cow absorb calcium. The composition of the present invention is in a liquid form and is preferably administered using a 200–300 cc drench gun. The end of the dispensing tube of the drench gun is placed between the teeth and cheek of the cow near the receptors that stimulate the esophageal groove reflex. A feature near the end of the dispensing tube causes a bulge in the cow's cheek which indicates the position of the dispensing tube within the cow's mouth. The composition stimulates the receptors and closes the esophageal groove, thereby allowing the liquid into the omasum where calcium is absorbed quicker than in the rumen. The cow swallows the liquid mixture in a near normal manner which prevents the solution from causing aspiration pneumonia.

24 Claims, 3 Drawing Sheets

FIG. 3

VETERINARY PHARMACEUTICAL METHOD OF ADMINISTRATION

CROSS-REFERENCE TO RELATED APPLICATIONS

This application is a continuation-in-part under 37 CFR 1.53(b)(1) of application Ser. No. 08/599,021, filed Feb. 08, 1996, status pending.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention

The present invention relates, generally to veterinary pharmaceutical and feed supplement compositions and to methods of administering the compositions. More particularly, the invention relates to a composition of calcium, B-vitamins and propylene glycol and to a method of orally administering or dispensing the composition to a recently freshened dairy cow.

2. Background Information

The process of a cow giving birth to a calf is called "freshening" in the dairy industry. The first milk or colostrum of a fresh cow has a high level of calcium and antibodies to benefit the newborn calf's immune system. The calcium found in the colostrum is taken from the bloodstream, thus lowering the serum calcium level of the cow, and is replaced either by intestinal calcium absorption or by bone calcium resorption. Calcium replacement is a special concern in today's dairy industry because fresh cows are milked soon after freshening, and thus can lose a considerable amount of calcium.

Low serum calcium levels in the blood of freshening cows can cause hypocalcemia, commonly referred to as milk fever. Hypocalcemia occurs because calcium enters the mammary gland faster than it is replaced. A cow suffering from milk fever will typically stagger and have cold ears. However, even though freshening cows do not show symptoms of milk fever, they still may develop typically asymptomatic subclinical milk fever.

The normal level of serum calcium in a cow's blood is 8.0 mg/100 cc of blood. Subclinical milk fever occurs when the serum calcium level drops below 7.5 mg/100 cc. The cow's rumen shuts down at 6.0 mg/100 cc and the cow is down at 4.0 mg/100 cc. Other problems related to low serum calcium levels include a displaced abomasum, slow calving, a retained placenta, ketosis, downer cow syndrome, uterine prolapse, and metritis. Milk fever and the other problems associated with low serum calcium can be prevented in freshening cows by keeping serum calcium in the blood at or above the level of 7.5 mg/100cc of blood. Should a cow develop subclinical milk fever, it is extremely important to treat the cow immediately both to prevent the serum calcium levels from dropping further and to quickly raise the serum calcium back to near normal levels.

In the past, various devices and/or methods have been used to raise serum calcium levels in freshening cows. These include intravenous dosing, gel tube solutions placed into the mouth with a caulking gun, and liquid solutions poured into the cow's mouth from a bottle. However, these devices and methods have significant limitations and shortcomings.

Dry Feed Supplements may contain calcium chloride and other minerals. These supplements are fed to an entire herd, often weeks before they freshen. See Goff (Journal of Dairy Science, 77 no. 4, April 1994, 1451–1456) and Moore (U.S. Pat. No. 5,556,634). Therefore, dry feed supplements are not an efficient treatment for an individual freshening cow.

Intravenous dosing (IV) is generally administered by a veterinarian. It is time consuming due to the importance of a slow administration rate. It also tends to spike the blood with a large amount of calcium. The cow responds to the spike by releasing a hormone called calcitonin that temporarily prevents the cow from naturally restoring its own serum calcium levels. Relapse can occur within 12 hours after an IV calcium treatment. Thus, IV dosing tends to be a temporary solution and, therefore, is not good for milk fever prevention. Furthermore, IV treatments shock the cow's system, stress the animal, and may even cause death.

Gel tubes are difficult to administer. The gel is forced from a caulking gun and is placed over the cow's tongue. A 300 cc dose of gel contains about 50 grams of calcium in the form of 150–200 grams of calcium chloride. This high amount of calcium chloride gives the gel a harsh salty taste. The cow's natural reflex is to cough out the bad tasting substance, resulting in considerable waste. Furthermore, the high levels of calcium chloride in the gel can cause acidosis and can irritate the throat, both of which can limit additional feedings if the first feeding does not produce the desired results. Additionally, forcing the gels over the tongue excites the cow, which has been shown to reduce calcium absorption. The harsh tasting gels enter into the rumen rather than the omasum, which is not desirable because the rumen absorbs calcium slower than the omasum. This slow rate of absorption encourages using higher levels of calcium chloride in the gels which, as addressed above, causes acidosis and irritation. Furthermore, an excited cow can inhale the product into its lungs, which may result in aspiration pneumonia and death.

Liquid calciums are orally administered calcium solutions that typically consist of calcium chloride, potassium, magnesium, phosphorous and water. They are usually administered by pouring the liquid into a cow's mouth using a long-necked bottle. As with the gels, the cow becomes excited and is at risk of aspirating the fluid, which may result in pneumonia and death. Because of this danger, the known art teaches away from using liquid compositions in favor of using viscous gels or dry feed supplements in spite of the fact that the liquid compositions are generally absorbed faster (Goff, page 1454, col. 1 line 1 to col. 2 line 6). Conventional liquid calciums also contain a high level of calcium chloride, typically 150–200 grams in a 300 to 400 cc dose. Therefore, a dose of conventional liquid calciums can cause acidosis and irritate the throat. Furthermore, forcing a cow's mouth open, inserting a long neck bottle, and pouring the fluid into the cow's mouth excites the cow because it is not a natural swallowing action. Therefore, this method fails to stimulate receptors in the mouth and pharynx to close the cow's esophageal groove and to allow the liquid calcium to enter and be quickly absorbed in the omasum. Additionally, these conventional liquid calciums do not contain vitamins or carriers, such as propylene glycol, to improve the effectiveness of the calcium solution.

Problematic side-affects for the above-mentioned treatments include their tendency to cause the freshening cow to lose its appetite at a time when proper nourishment is vital. A well-nourished cow is less likely to develop milk fever, ketosis, a displaced abomassum or a retained placenta, and is more likely to quickly recover from the effects of low serum calcium levels. Furthermore, the high levels of calcium chloride used by the known art are associated with severe and fatal risks, including metabolic acidosis, loss of appetite, and irritation/ulceration of the mouth and throat (Goff, page 1455, column 1, lines 3–25).

It is a general object of this invention to provide a milk fever treatment and preventative for cows which overcomes the limitations and shortcomings of the known art described above.

It is a further object of this invention to provide a calcium treatment for cows which does not cause the cow to lose its appetite, but rather stimulates the cow's appetite.

It is a further object of this invention to provide a calcium treatment for cows which does not shock the cow's system.

It is a further object of this invention to provide an oral calcium treatment which stimulates the esophageal groove reflex, thereby allowing the composition into the omasum rather than in the rumen.

It is a further object of this invention to provide an oral calcium treatment for cows which reduces the risk of acidosis.

It is a further object of this invention to provide an oral calcium treatment for cows which does not irritate the throat.

It is a further object of this invention to provide an oral calcium treatment for cows which is not harsh or bitter tasting.

It is a further object of this invention to provide an oral calcium treatment for cows which provides additional nutritional benefits to the cow.

It is a further object of this invention to provide a calcium treatment for cows which is easy to administer.

It is a further object of this invention to provide an oral calcium treatment for cows which reduces the risk of aspiration pneumonia.

It is a further object of this invention to provide an oral calcium treatment for cows which does not excite the cow.

It is a further object of this invention to provide an oral calcium treatment for cows which is not administered between the teeth and over the tongue.

It is a further object of this invention to provide an oral calcium treatment for cows which can be administered with a drench gun.

BRIEF SUMMARY OF THE INVENTION

The present invention provides a liquid composition for preventing and treating milk fever in freshening cows, and a method of administering that composition. The basic composition is a mixture of water, calcium chloride, propylene glycol, B vitamins and minerals. A relatively low calcium content is provided by an effective concentration of calcium chloride. The propylene glycol is a carrier that aids in the dispersion of the calcium into the blood stream, and gives the cow an energy boost. The B vitamins stimulate the cow's appetite. The minerals help the cow absorb calcium and replace the minerals that are used to make the colostrum.

The composition of the present invention is in a liquid form and is preferably administered using a 200–300 cc drench gun. The end of the dispensing tube of the drench gun is placed between the teeth and cheek of the cow. The drench gun tube has a feature, such as a curved tube or a bend in the end of the tube, that ensures that the tube is properly positioned toward the back of the mouth of the cow. This feature causes an externally visible bulge in the cow's cheek. A properly positioned dispensing tube allows the cow to remain calm and to swallow a dispensed solution in a near normal manner, thus preventing the solution from being inhaled by an excited cow and causing aspiration pneumonia. The near normal swallowing action of the composition stimulates receptors to close the esophageal groove, thereby allowing the liquid to enter the omasum where calcium is absorbed quicker than in the rumen where other calcium treatments are typically absorbed. Because of the faster and better absorption in the omasum, calcium dosages in the present invention are lower and more effective than calcium dosages found in conventional treatments.

Significant features of the composition include the incorporation of the B vitamins, the low levels of calcium chloride, and its liquid form. A significant feature of the method of administration is that a tube is placed between a cow's teeth and cheek, thus allowing the cow to remain calm when liquid is dispensed near the receptors that invoke the esophageal groove reflex. These receptors are found in the cow's mouth and pharynx.

The B vitamins stimulate appetite in freshening cows, which is desirable because a well-nourished cow is less likely to develop milk fever, ketosis, a displaced abomasum or a retained placenta. Additionally, the composition uses considerably lower levels of calcium in the form of calcium chloride than has ever been used or suggested to prevent or treat milk fever in cows. The use of lower levels of calcium chloride eliminates the severe and fatal risks associated with higher levels of calcium chloride, including metabolic acidosis, loss of appetite, and irritation/ulceration of the mouth and throat. Furthermore, liquid drenches are quicker, cheaper, more effective and more efficient at preventing and treating milk fever than dry feed supplements or gels. Because the cow absorbs the composition quickly, the effectiveness of a treatment can be observed in the eating habits and the overall physical appearance of the cow, including whether the cow is up or down and whether the cow appears sharp and healthy or slow and depressed. The calcium chloride concentration, the liquid form, and the method of administration all contribute to stimulating the esophageal groove reflex. The composition enters the omasum and raises the serum calcium levels to near normal levels within 10 to 15 minutes when the esophageal groove is closed.

The features, benefits and objects of this invention will become clear to those skilled in the art by reference to the following description, claims and drawings.

DETAILED DESCRIPTION

Composition

1. Preferred Embodiment.

The present invention provides a low-viscosity liquid composition and method of administration for preventing and treating milk fever in freshening cows. The composition generally comprises water, calcium chloride, propylene glycol, magnesium chloride, potassium chloride, and B-vitamins, including riboflavin supplement, vitamin B12 supplement, thiamin HCL, pyridoxine HCL, and D-calcium pantothenate.

The calcium provided in this composition quickly raises the serum calcium level in the blood of freshening cows. Effective ranges of calcium, and the corresponding ranges of calcium chloride, are shown in Table 1 in terms of both percent by weight for a 200 cc dose and in terms of grams.

TABLE 1

|  | Effective Range | Particular Range | Preferred |
|---|---|---|---|
| Ca (% by weight) | 5 to 20% | 9 to 16% | 12.7% |
| Ca (g) | 10 to 40 grams | 18 to 32 grams | 25.4 grams |
| CaCl$_2$ (% by weight) | 14 to 56% | 25 to 44% | 35% |
| CaCl$_2$ (g) | 28 to 112 grams | 50 to 88 grams | 70 grams |

Calcium chloride is an economical means of providing calcium in the solution. However, it is anticipated that the calcium could be provided by other sources. Other calcium sources include calcium proportionate, calcium oxide, and calcium sulfate. Calcium proportionate raises serum calcium levels slower than calcium chloride but the effects tend to last longer.

The amount of calcium in the present invention is lower than in other calcium solutions, which typically range from 40 to 55 g/per 300–400cc dose. Both the composition and the method of administering the composition of the present invention stimulate the esophageal groove reflex and allow the liquid to enter the omasum where it is absorbed more quickly than if it entered the rumen. Other calcium treatments tend to enter the rumen and are absorbed more slowly. The lower level of calcium chloride also has the added benefits of being less likely to cause acidosis and less likely to irritate the cow's throat. Therefore, additional treatments may be given if the first treatment is not successful. Table 2 compares amounts of calcium chloride and calcium in the composition of the present invention to typical gel tubes and liquid calcium supplements.

TABLE 2

|  | Present Invention | Liquid Drenches | Gel Tubes |
|---|---|---|---|
| Dose | 200 cc * | 300 to 400 cc | 300 cc |
| Calcium Chloride | 70 grams | 150 to 200 grams | 150 to 200 grams |
| Calcium | 25.4 grams | 40 to 55 grams | 49 to 55 grams ** |

\* The present invention can be administered in doses of up to 300 cc in which an effective amount of calcium is distributed by a smaller percent by weight.
\*\* Although gel tubes are also available in 100 grams, the majority of tubes that are sold are in the 49–55 grams range.

The composition of the present invention, as displayed in Table 1 and Table 2, has successfully balanced the opposing demands of having an effective amount of calcium to raise the serum calcium levels, an effective concentration of calcium chloride to stimulate the esophageal reflex, and an effective amount of calcium chloride to prevent acidosis.

The propylene glycol gives the cow an energy boost and also gives the composition a sweet taste to encourage the cow to swallow it rather than fight it or spit it out. Both the propylene glycol and the concentration of the calcium chloride contribute to the normal swallowing action of the cow and the closing of the esophageal groove. The amount of propylene glycol in the liquid composition ranges from 1% to 25% by weight, and more particularly the amount is from 5 to 10% by weight, with 7% being preferred.

The magnesium chloride and potassium chloride provide the minerals magnesium and potassium, which replace minerals used to make the colostrum and help the cow absorb calcium. The amount of magnesium chloride in the liquid composition ranges from 0.05% to 10% by weight, with 1.67% being preferred. The amount of potassium chloride in the liquid composition ranges from 0.01% to 1% by weight with 0.72% being preferred.

Loss of appetite is a common problem with the calcium treatments of the known art. A well nourished cow is less likely to develop milk fever, ketosis, displaced abomasum or retained placenta. The liquid composition includes B vitamins to stimulate the cow's appetite. The composition contains riboflavin, vitamin B12, thiamin HCL, pyridoxine HCL and D-calcium pantothenate collectively within a range of 0.005% to 0.1% by weight. Preferably, each element is present in an amount of about 0.0239% by weight.

Table 3 shows the elements and their effective range, a more particular range, and their preferred concentrations.

TABLE 3

| Ingredient | Effective Range (% By Weight) | Particular Range (% By Weight) | Preferred (% By Weight) |
|---|---|---|---|
| Water | — | 50 to 60% | — |
| Calcium Chloride | 14 to 56% | 25 to 44% | 35% |
| Pure Calcium | 5 to 20% | 9 to 16% | 12.7% |
| Propylene Glycol | 1 to 25% | 5 to 10% | 7% |
| B-Vitamins | 0.005 to 0.1% | — | — |
| Riboflavin | — | — | 0.0239% |
| Vitamin B12 | — | — | 0.0239% |
| Thiamin HCL | — | — | 0.0239% |
| Pyridoxine HCL | — | — | 0.0239% |
| D-Calcium | — | — | 0.0239% |
| Mag. Chloride | — | 0.05 to 10% | 1.67% |
| Potassium Chloride | — | 0.01 to 1% | 0.72% |

A significant feature of the composition is its liquid form. Liquid drenches are quicker, more effective and more efficient at preventing and treating milk fever than dry feed supplements or gels. The liquid form allows the composition to enter and be directly absorbed by the cow's omasum, and thus quickly and effectively raise the serum calcium level of the cow in 10 to 15 minutes. Furthermore, liquid drenches cost a third of the cost of anionic salts. Additionally, the liquid composition provides for easier observation and assurance of the effectiveness of a treatment because the cow absorbs the liquid form quicker than dry compositions. The effectiveness of a treatment can be observed in the eating habits and the overall physical appearance of the cow, including whether the cow is up or down and whether the cow appears sharp and healthy or slow and depressed. On the other hand, dry compositions are evaluated by measuring the pH in the cow's urine, a difficult and time-consuming task for farmers. In spite of these benefits of liquid drenches, the known art teaches away from the use of liquid compositions because of the risk for aspiration pneumonia.

2. First Alternate Embodiment.

Table 4 displays the ingredients of a first alternate embodiment that may be added to the preferred embodiment to provide additional benefits to the freshening cow.

TABLE 4

| Ingredient | Range | Preferred | Purpose |
|---|---|---|---|
| Selenium | 0.1 to 3.0 mg. per 200 cc dose | 1.5 mg per 200 cc dose | Increase the immune response. |
| Cobalt | 7.5 to 750 ppm | 350 ppm | Aids the absorption and use of Vitamin B12. |

TABLE 4-continued

| Ingredient | Range | Preferred | Purpose |
| --- | --- | --- | --- |
| Vitamin E | 10 to 10,000 I.U. per 200 cc dose | 1,000 I.U per 200 cc dose | Increase the immune response. |
| Magnesium | 0.05 to 10% by weight | 1.67% by weight | Prevent grass tetany. |
| Calcium Propionate | 5 to 95 grams | 10 to 47.5 grams | Additional source of calcium and energy. |
| Flavoring (e.g. root beer) | — | — | Improve the taste of the liquid. |

3. Second Alternate Embodiment.

Table 5 displays the ingredients and quantities of another composition that can be added to the composition of the preferred or the first alternate embodiments to prevent and treat Ketosis. That composition is preferably prepared and mixed in equal amounts with a composition of the preferred embodiment or a composition of the first alternate embodiment. Maximum, minimum and preferred quantities listed are for a 200 cc volume.

TABLE 5

| Ingredient | Range | Preferred | Purpose |
| --- | --- | --- | --- |
| Propylene Glycol | 1 to 500 g | 180 g | Energy Boost |
| Niacin | 5 to 14 g | 10 g | Ketosis Treatment |
| Vitamin A | 55,000 to 900,000 I.U. | 420,000 I.U. | Immune Stimulant |
| Vitamin B2 | 3 to 500 mg | 48 mg | Appetite Stimulant |
| Vitamin B6 | 4 to 200 mg | 60 mg | Appetite Stimulant |
| Vitamin B12 | 45 to 1000 Mcg | 600 Mcg | Appetite Stimulant |
| D-CAL Pantothenate | 15 to 500 mg | 180 mg | Appetite Stimulant |
| Folic Acid | 0.5 to 20 mg | 2.8 mg | Appetite Stimulant |
| Vitamin C | 15 to 920 mg | 180 mg | Immune Stimulant |
| Vitamin D3 | 10,000 to 900,000 I.U. | 84,000 I.U. | Help Absorb Calcium |
| Vitamin E | 5 to 950 I.U. | 100 I.U. | Immune Stimulant |

Method Of Administering Compositions

Figure 1A:
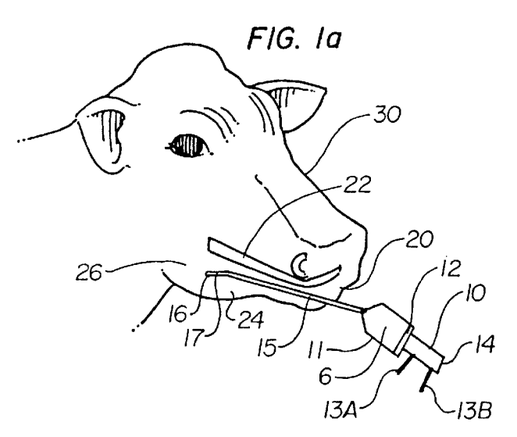
FIG. 1A is an illustration of a dispenser having a bent tube feature used to administer the solution in a cow's mouth.
Figures 1B, 1C:
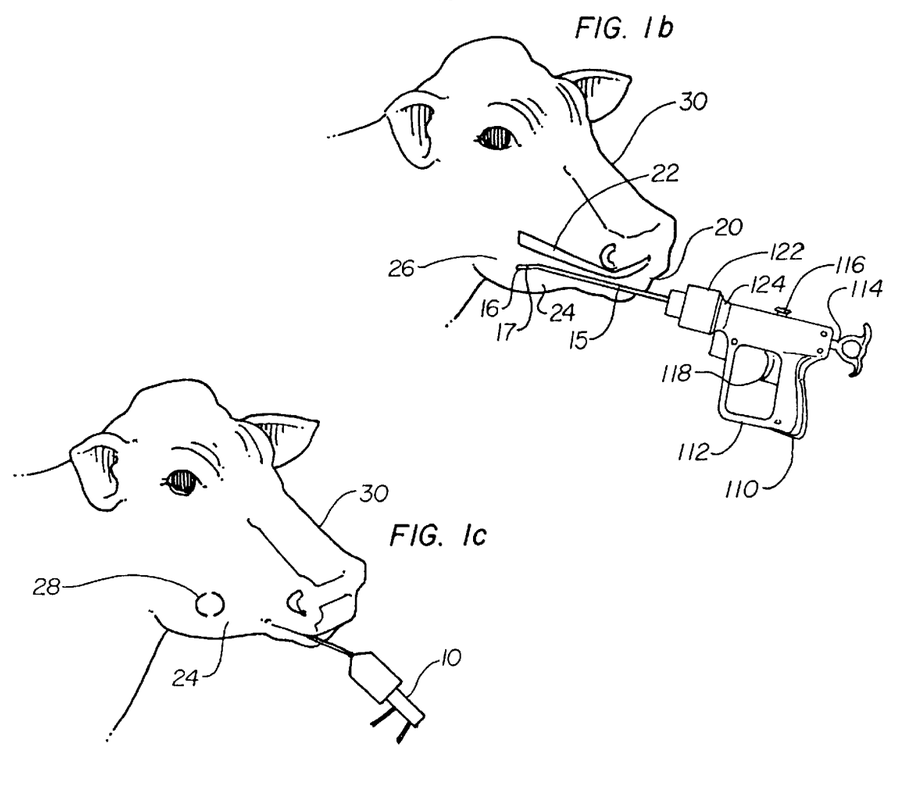
FIG. 1B is an illustration of a dispenser having a curved tube feature used to administer the solution in a cow's mouth.
FIG. 1C is an illustration showing the external bulge in the cow's cheek caused by the tube feature.

Referring to the drawings, wherein like reference numerals designate like or similar elements throughout, a preferred method of administering compositions of the present invention is illustrated in FIGS. 1A, 1B, and 1C.

Referring to FIGS. 1A and 1B, a dispenser 10 or 110 is used to administer compositions of the present invention into the mouth 20 of a cow 30. The dispenser is preferably a 200–300 cc drench gun. The drench gun 10 is loaded with a liquid composition 6 and is positioned so that the dispensing tube 15 is inserted in a cow's mouth 20 between the teeth 22 and cheek 24. The dispensing tube 15 is preferably placed such that its entire length, generally 7–10 inches, is within the mouth 20 and the end 16 of tube 15 is at or near the back 26 of cheek 24.

Referring to FIG. 1C, a bulge 28 in the cheek 24 of the cow 30 is externally visible and indicates that the tube 15 is in the proper position within the cow's mouth. The bulge 28 is caused by a feature, such as a bent section 17a in FIG. 1A or a curved section 17b in FIG. 1B, of the end 16 of dispensing tube 15. The composition is administered at a rate of about 20 to 50 cc per second, with the head of the cow somewhat raised. The cow can swallow in an unexcited or near normal manner with this method of administration, thus reducing the risk of aspiration pneumonia. Furthermore, this method of administration dispenses the composition near the receptors that invoke the esophageal groove reflex.

Referring to FIG. 1A, liquid 6 is dispensed from the dispenser through a dispensing tube 15 by manually compressing spring-loaded levers 13A and 13B on a handle 14. These levers 13A and 13B push a piston 12 down a cylinder 11 to force the liquid 6 out of the cylinder 11 and into the dispensing tube 15.

Figure 2:
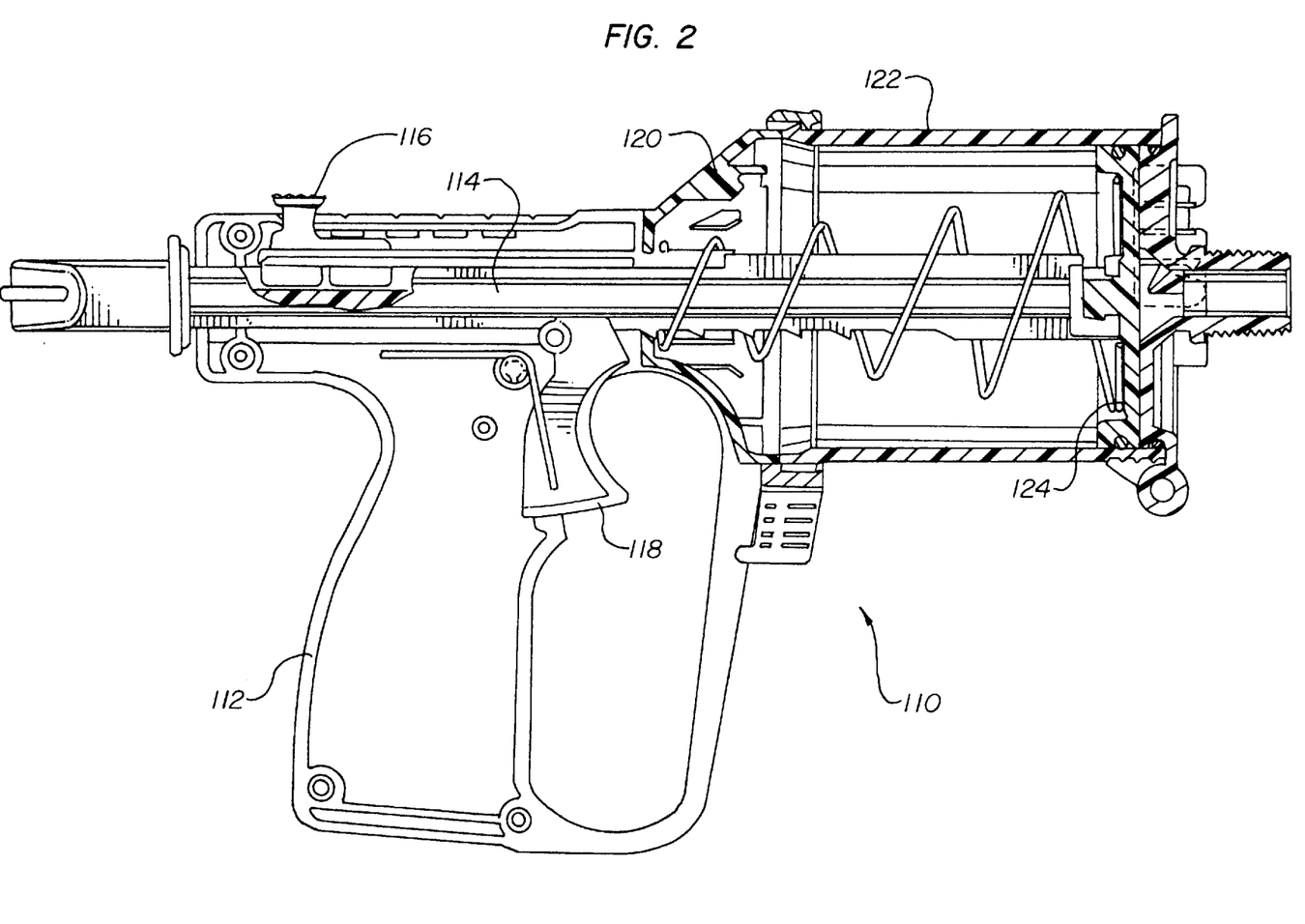
FIG. 2 is a cross-sectional side view of a preferred dispenser used to administer the solution to a cow.

A preferred dispenser, or drench gun, is shown in FIGS. 1B and 2. This drench gun is the subject of Applicant's U.S. Utility patent application Ser. No. 08/880,891 filed Jun. 23, 1997, which is based on Applicant's U.S. Provisional Patent Application Ser. No. 60/025,904 filed Sep. 11, 1996, and is hereby incorporated by reference. Referring to FIG. 2, the gun 110 generally comprises a handle 112, a shaft 114, a fill limiter 116, a dispensing limiter 118, a cone 120, a cylinder 122, a piston 124, and an end cap 126. The piston 124 is attached to an end of the shaft 114 and provides a moveable seal within the cylinder 122. The fill limiter 116 is adjustably attached to the handle 112 and interacts with the shaft 114 to limit the distance that both the shaft 114 and piston 124 can be retracted. Thus, adjusting the fill limiter 116 modifies the capacity of the cylinder 122 as determined by the retracted position of the piston 124. In a preferred embodiment, the fill limiter 116 is adjustable in 50 cc dose intervals. The dispensing limiter 118 interacts with a set of notches on the shaft 114 in such a manner as to move both the shaft 114 and piston 124 forward to expel a predetermined dose of fluid when it is actuated and to prevent the shaft 114 from moving forward when it is not actuated. In a preferred embodiment, the dispensing limiter 118 and shaft 114 are constructed and arranged to dispense fluid in 50 cc doses. The cone 120 provides an interface between the handle 112 and the replaceable cylinder 122. The gun 110 can accommodate different drench dosages by replacing the cylinder 122 with one of a different size. Furthermore, the shaft 114 can be replaced with one having a different set of notches that correspond with a different dispensing interval. The end cap 126 mounts onto the end of the cylinder 122. It preferably includes a piercing member designed to puncture a bladder, packet, or other liquid container within the cylinder 122 upon the application of pressure by the piston 124. Additional pressure applied by the piston 124 expels the liquid out of the container through an outlet in the end cap 126. Alternatively to using pre-packaged bags in the cylinder 122, the drench gun could draw fluid from a bulk container.

Referring to FIG. 1C, a cow 30 objects less to having the tube 15 placed between its teeth 22 and its cheek 24 than if the tube 15 is forced between its upper and lower teeth 22. The cow 30 swallows the composition in a near-normal manner, thereby nearly eliminating the danger of pneumonia and death caused by aspirating the composition into the cow's lungs. This method of administration prevents the cow 30 from becoming excited and it stimulates the esophageal groove reflex, thereby allowing the calm cow to absorb calcium better and to quickly attain near normal serum calcium levels. This simple method of administration does not require a veterinarian.

Figure 3:
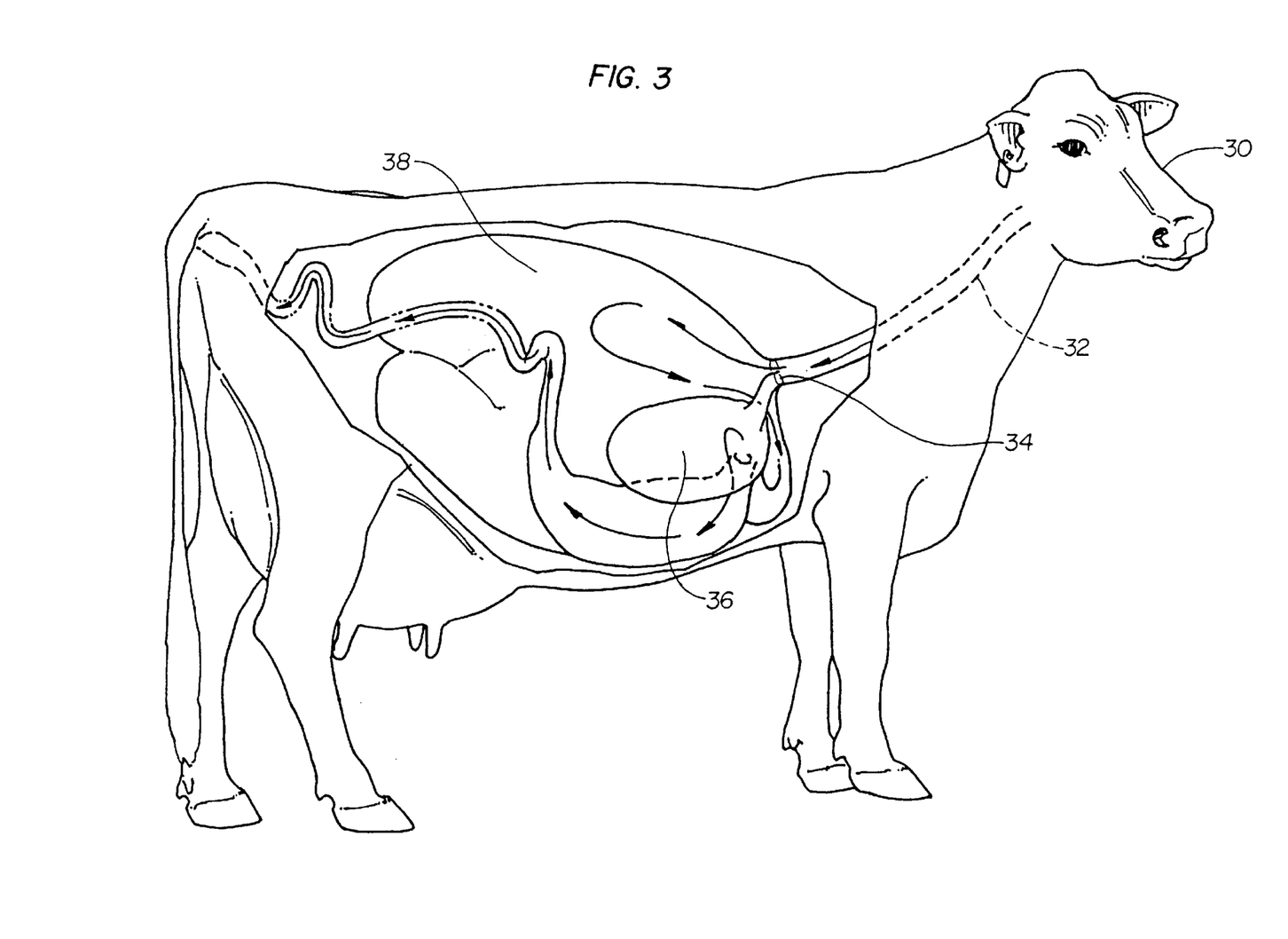
FIG. 3 is an illustration of the digestive system of a cow.

Referring to FIG. 3 because there is minimal irritation in the esophagus 32, a normal swallowing action takes place and the esophageal groove 34 can close allowing the composition to enter the omasum 36. This is desirable because absorption of the composition is faster and more effective in the omasum 36 than in the rumen 38. Other calcium treatments enter the rumen 38 where the calcium is absorbed slowly. Thus, the composition of the present invention uses lower amounts of calcium to provide a quick, effective and efficient treatment. As such, the composition and method of administration of the present invention is an excellent treatment for individual freshening cows at risk of developing milk fever.

Testing

In order to determine the effectiveness of the preferred composition and the method of administration, blood tests were performed on freshening Jersey cows in Wisconsin within 2–4 hours of freshening. Blood samples were drawn from the subject cows three times: once just before administering a mixture of the preferred composition; once 15 minutes after administering it; and once 30 minutes after administering it. The blood samples were analyzed for serum calcium content by the laboratory of Myrtle Worth Medical Center, 2321 Stout Road, Menomonie, Wis. 54751. Table 6 lists the results.

TABLE 6

Measured Serum Calcium Levels
(mg of calcium per 100 cc of blood)
With Respect to the Time of
Administering the Composition to the Cow

| Cow Number | Before | 15 Minutes After | 30 Minutes After |
| --- | --- | --- | --- |
| 32 | 7.6 | 9.6 | 9.8 |
| 69 | 6.3 | 10.1 | 9.8 |
| 10 | 5.9 | 8.3 | 8.1 |
| 66 | 4.6 | 5.8 | 5.8 |
| 40 | 6.0 | 8.0 | 8.5 |
| 44 | 7.9 | 8.8 | 8.9 |
| 77 | 7.4 | 10.5 | 10.8 |
| E | 6.7 | 8.3 | 7.7 |
| 68 | 8.5 | 10.9 | 10.6 |
| 1 | 8.5 | 9.8 | 9.9 |
| 2 | 6.0 | 8.0 | 8.5 |

Normal calcium level = 8.0 mg/100 cc of blood.
Subclinical calcium level = 7.5 & lower mg/100 cc of blood.
Rumen shuts down = 6.0 mg/100 cc of blood.
The cow is down at 4.0 mg/100 cc of blood.

Similar blood tests were performed on freshening Holstein cows in Arizona within 2–4 hours of freshening in order to determine the effectiveness of the preferred composition and method of administration on a different breed of cow. Table 7 lists those results.

TABLE 7

Measured Serum Calcium Levels
(mg of calcium per 100 cc of blood)
With Respect to the Time of
Administering the Composition to the Cow

| Cow Number | Before | 15 Minutes After | 30 Minutes After |
| --- | --- | --- | --- |
| A | 8.2 | 9.4 | 9.6 |
| B | 5.9 | 6.9 | 6.9 |
| C | 6.9 | 8.3 | 8.4 |
| D | 7.0 | 8.9 | 9.3 |
| E | 8.0 | 8.9 | 9.0 |

Normal Calcium level = 8.0 mg/100 cc of blood.

These tests show that the preferred composition administered in the preferred method of this invention quickly and effectively raises serum calcium levels within 15 minutes of administration. The time immediately following freshening is most critical because, once the serum calcium levels begin to drop into the subclinical milk fever range (below 7.5 mg/100 cc), the cow can quickly develop milk fever, have its rumen shut down, and develop the other complications enumerated above with regards to low serum calcium levels. Therefore, it is vitally important to the health of the cow to stop the downward trend and quickly restore the serum calcium levels to a near normal level, or at least to a level that eliminates the danger of the rumen shutting down. These tests show that a recently freshened cow can be individually treated with the preferred composition using the preferred method of administration to quickly, efficiently, and effectively raise the serum calcium levels, and thus treat a cow suffering with milk fever or prevent a cow from developing milk fever. The cow's natural ability to produce calcium recovers once the critical stage is passed. Therefore, a one-time treatment is often all that is necessary. However, multiple treatments can be given if necessary because the low level of calcium chloride found the present invention does not cause acidosis or irritate the throat.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. A method of administering an oral liquid calcium supplement to a cow comprising the steps of:
   (a) placing an amount of the liquid calcium supplement in a dispenser, the dispenser having a tube with a dispensing end;
   (b) positioning the tube in a cow's mouth such that the tube is inserted between the cow's teeth and cheek and the dispensing end is near the cow's receptors at the back of the cheek that invoke an esophageal groove reflex, whereby the cow remains unexcited by the positioning of the tube between the teeth and cheek; and
   (c) dispensing a prophylactically effective amount of the liquid calcium supplement into the cow's mouth through the dispensing end of the tube, the dispensed supplement stimulating the receptors which invoke the esophageal groove reflex allowing the supplement to enter the omasum and to quickly, effectively, and efficiently treat milk fever in a freshening cow, whereby the cow remains unexcited as it swallows the dispensed supplement.

2. The method of administering an oral liquid calcium supplement to a cow of claim 1, wherein the liquid calcium supplement is expelled at a rate that enables the cow to swallow the liquid calcium supplement in a substantially natural manner.

3. The method of administering an oral liquid calcium supplement to a cow of claim 2, wherein the rate is between 20 and 50 cc per second.

4. The method of administering an oral liquid calcium supplement to a cow of claim 1, wherein the tube has a feature near the dispensing end, wherein the feature causes the cow's cheek to bulge, thereby providing an externally visible reference for said step of positioning the tube in the cow's mouth.

5. The method of administering an oral liquid calcium supplement to a cow of claim 4, wherein the feature is a bend in the tube.

6. The method of administering an oral liquid calcium supplement to a cow of claim 4, wherein the feature is a curved shape in the tube.

7. The method of administering an oral liquid calcium supplement to a cow of claim 1, wherein the liquid calcium supplement comprises:
   (a) water;
   (b) propylene glycol; and
   (c) an amount of calcium between 10 and 40 grams.

8. The method of administering an oral liquid calcium supplement to a cow of claim 7, wherein the amount of calcium is between 18 and 32 grams.

9. The method of administering an oral liquid calcium supplement to a cow of claim 8, wherein the amount of calcium is approximately 25.4 grams.

10. The method of administering an oral liquid calcium supplement to a cow of claim 1, wherein the liquid calcium supplement comprises:
    (a) water;
    (b) propylene glycol; and
    (c) an amount of calcium between 5% and 20% by weight.

11. The method of administering an oral liquid calcium supplement to a cow of claim 10, wherein the amount of calcium is between 9% and 16% by weight.

12. The method of administering an oral liquid calcium supplement to a cow of claim 11, wherein the amount of calcium is approximately 12.7% by weight.

13. The method of administering an oral liquid calcium supplement to a cow of claim 10, wherein the amount of calcium is provided by an amount of calcium chloride between 14% and 56% by weight.

14. The method of administering an oral liquid calcium supplement to a cow of claim 10, wherein the liquid calcium supplement further comprises an amount of B vitamins.

15. The method of administering an oral liquid calcium supplement to a cow of claim 10, wherein the liquid calcium supplement further comprises an amount of magnesium chloride and an amount of potassium chloride.

16. The method of administering an oral liquid calcium supplement to a cow of claim 10, wherein the liquid calcium supplement further comprises selenium, cobalt, magnesium, calcium propionate, and flavoring.

17. The method of administering an oral liquid calcium supplement to a cow of claim 10, wherein the liquid calcium supplement further comprises niacin, vitamin A, vitamin B2, vitamin B6, vitamin B12, D-calcium pantothenate, folic acid, vitamin C, vitamin D3, and vitamin E.

18. The method of administering an oral liquid calcium supplement to a cow of claim 17, wherein the liquid calcium supplement further comprises selenium, cobalt, magnesium, calcium propionate, and flavoring.

19. The method of administering an oral liquid calcium supplement to a cow of claim 1, wherein said method is an individual prophylactic treatment for milk fever in a recently freshened cow.

20. The method of administering an oral liquid calcium supplement to a cow of claim 1, wherein the liquid calcium supplement has low viscosity.

21. The method of administering an oral liquid calcium supplement to a cow of claim 1, further comprising the step of forming the liquid calcium supplement, wherein the supplement comprises a mixture of water, propylene glycol and calcium.

22. A method of administering an oral liquid calcium supplement as an individual treatment for quickly and effectively raising serum calcium levels in the blood of a freshening cow to prevent and treat milk fever, the method comprising the steps of:
    (a) placing an amount of the liquid calcium supplement in a drench gun having a tube with a dispensing end, wherein the liquid calcium supplement comprises:
       (i) water;
       (ii) an amount of propylene glycol between 1% and 25% by weight; and
       (iii) an amount of calcium between 5% and 20% by weight;
    (b) positioning the tube in a cow's mouth such that the tube is inserted between the cow's teeth and cheek and the dispensing end is near the cow's receptors at the back of the cheek that invoke an esophageal groove reflex, whereby the cow remains unexcited by the positioning of the tube between the teeth and cheek; and
    (c) dispensing a prohylactically effective amount of the liquid calcium supplement through the dispensing end of the tube and into the cow's mouth, the dispensed supplement stimulating the receptors which invoke the esophageal groove reflex allowing the supplement to enter the omasum and to quickly, effectively, and efficiently treat milk fever in a freshening cow, whereby the cow remains unexcited as it swallows the dispensed supplement in a substantially natural manner.

23. The method of administering an oral liquid calcium supplement of claim 22, wherein the liquid calcium supplement comprises:
    (a) an amount of water between 50% and 60% by weight;
    (b) an amount of propylene glycol between 5% and 10% by weight; and
    (c) an amount of calcium between 9% and 16% by weight.

24. A method for administering an oral liquid calcium supplement to a recently freshened cow, comprising the steps of:
    (a) forming the liquid calcium supplement, wherein the supplement comprises:
       (i) water;
       (ii) propylene glycol; and
       (iii) calcium;
    (b) filling a dispenser with an amount of the liquid calcium supplement, the dispenser having a tube with an end;
    (c) positioning the tube in the cow's mouth between the cow's teeth and cheek, wherein the end of the tube is near the cow's receptors at the back of the cheek that invoke an esophageal groove reflex, whereby the cow remains unexcited by the positioning of the tube between the teeth and cheek; and (d) dispensing a prophylactically effective amount of the liquid calcium supplement into the cow's mouth through the end of the tube, the dispensed supplement stimulating the receptors which invoke the esophageal groove reflex allowing the supplement to enter the omasum and to quickly, effectively, and efficiently treat milk fever in a freshening cow, whereby the cow remains unexcited as it swallows the dispensed supplement in a substantially natural manner.

* * * * *